(12) United States Patent
Baum et al.

(10) Patent No.: US 8,318,959 B1
(45) Date of Patent: Nov. 27, 2012

(54) SYNTHESIS AND POLYMERIZATION OF GLYCIDYL ETHERS

(75) Inventors: Kurt Baum, Pasadena, CA (US); Wen-Huey Lin, Laguna Niguel, CA (US)

(73) Assignee: Flurochem, Inc., Azusa, CA (US)

( * ) Notice: Subject to any disclaimer, the term of this patent is extended or adjusted under 35 U.S.C. 154(b) by 0 days.

(21) Appl. No.: 13/343,132

(22) Filed: Jan. 4, 2012

(51) Int. Cl.
C07D 303/08 (2006.01)
C07D 303/36 (2006.01)
C07D 303/48 (2006.01)

(52) U.S. Cl. .................. 549/551; 549/558; 549/563

(58) Field of Classification Search .............. 549/551, 549/558, 563
See application file for complete search history.

(56) References Cited

U.S. PATENT DOCUMENTS

| | | | | |
|---|---|---|---|---|
| 3,557,181 | A * | 1/1971 | Lakritz et al. | 568/589 |
| 3,652,600 | A * | 3/1972 | Grakauskas | 549/551 |
| 3,784,420 | A * | 1/1974 | Frankel et al. | 149/22 |
| 3,832,390 | A * | 8/1974 | Frankel et al. | 560/227 |
| 3,907,907 | A * | 9/1975 | Frankel et al. | 568/589 |
| 4,011,117 | A * | 3/1977 | Lo et al. | 149/88 |
| 4,141,768 | A * | 2/1979 | Lo et al. | 149/19.3 |
| 4,168,273 | A * | 9/1979 | Witucki et al. | 549/516 |
| 4,341,712 | A * | 7/1982 | Frankel et al. | 552/11 |
| 5,120,827 | A | 6/1992 | Willer et al. | |
| 5,741,998 | A * | 4/1998 | Hinshaw et al. | 149/19.6 |
| 5,801,325 | A * | 9/1998 | Willer et al. | 149/19.4 |
| 6,706,849 | B2 | 3/2004 | Kim et al. | |
| 7,208,637 | B2 | 4/2007 | Kim et al. | |
| 7,427,687 | B2 | 9/2008 | Kim et al. | |

FOREIGN PATENT DOCUMENTS

| | | |
|---|---|---|
| DE | 2063 513 | 3/1973 |
| EP | 614862 A1 * | 9/1994 |
| GB | 1316692 A * | 5/1973 |

OTHER PUBLICATIONS

Milton B. Frankel and Edgar R. Wilson. Energetic Azido Monomers. J. Chem. Eng. Data 1981, 26, 219. 1981.*
Vytautas Grakauskas. Alkylation Reactions of 2-Fluoro-2,2-dinitroethanol. J . Org. Chern., vol. 56, No. 9, 1970.*
Vytautas Grakauskas. Polynitroalkyl Ethers. J. Org. Chem., vol. 38, No. 17, 1973.*
Bartok, et. al., "The Chemistry of Functional Groups, Supplement E. Part 2", S. Patai, ed. John Wiley & Sons, New York, 1980, Chap. 4, Oxiranes, pp. 610-627.
Beard, et. al., "Synthesis of Some Novel Trifluoromethanesulfonates and their Reactions with Alcohols", J. Org. Chem. 1973, 38:3673-3677.
A. E. Oberth, "Functionality determination in Hydroxyl-terminated Prepolymers", AIAA 16 th Aerospace Sciences Meeting Huntsville, AL Jan. 1978.
Willer, et. al., "Poly(Glycidyl Nitrate) and Poly(Glycidyl Nitrate) Propellants", 1990 JANNAF Propulsion Meeting, CPIA Publication 550, 3:223-230.
Willer, et. al., "Poly(Glycidyl Nitrate) Revisited", Proceedings of the APDA Joint International Symposium on the Compatibility of Plastics and Other Materials with Explosives, Propellants and Ingredients, American Defense Preparedness Association, Oct. 1989, 258-269.

* cited by examiner

*Primary Examiner* — Randy Gulakowski
*Assistant Examiner* — Mike M Dollinger
(74) *Attorney, Agent, or Firm* — Joseph E. Mueth

(57) ABSTRACT

The method of preparing novel allyl ethers.
Novel glycidyl ethers and their preparation.
Polyfunctional poly(glycidyl ethers) their methods of preparation.
Novel polyurethanes based on the polyfunctional glycidyl ethers and their method of preparation.

4 Claims, 9 Drawing Sheets

Figure 1. Qualitative test for high molecular weight polyurethane.

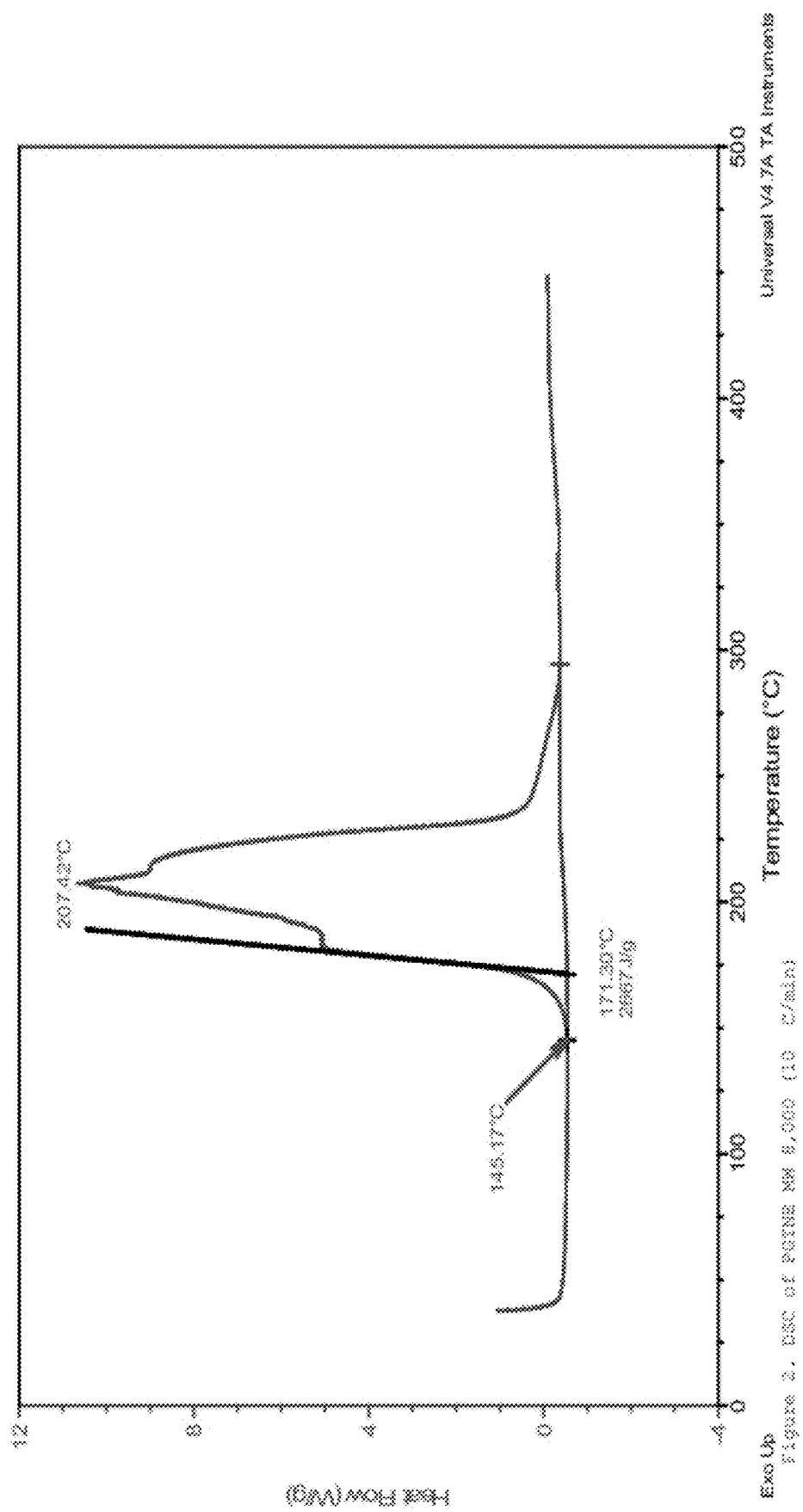

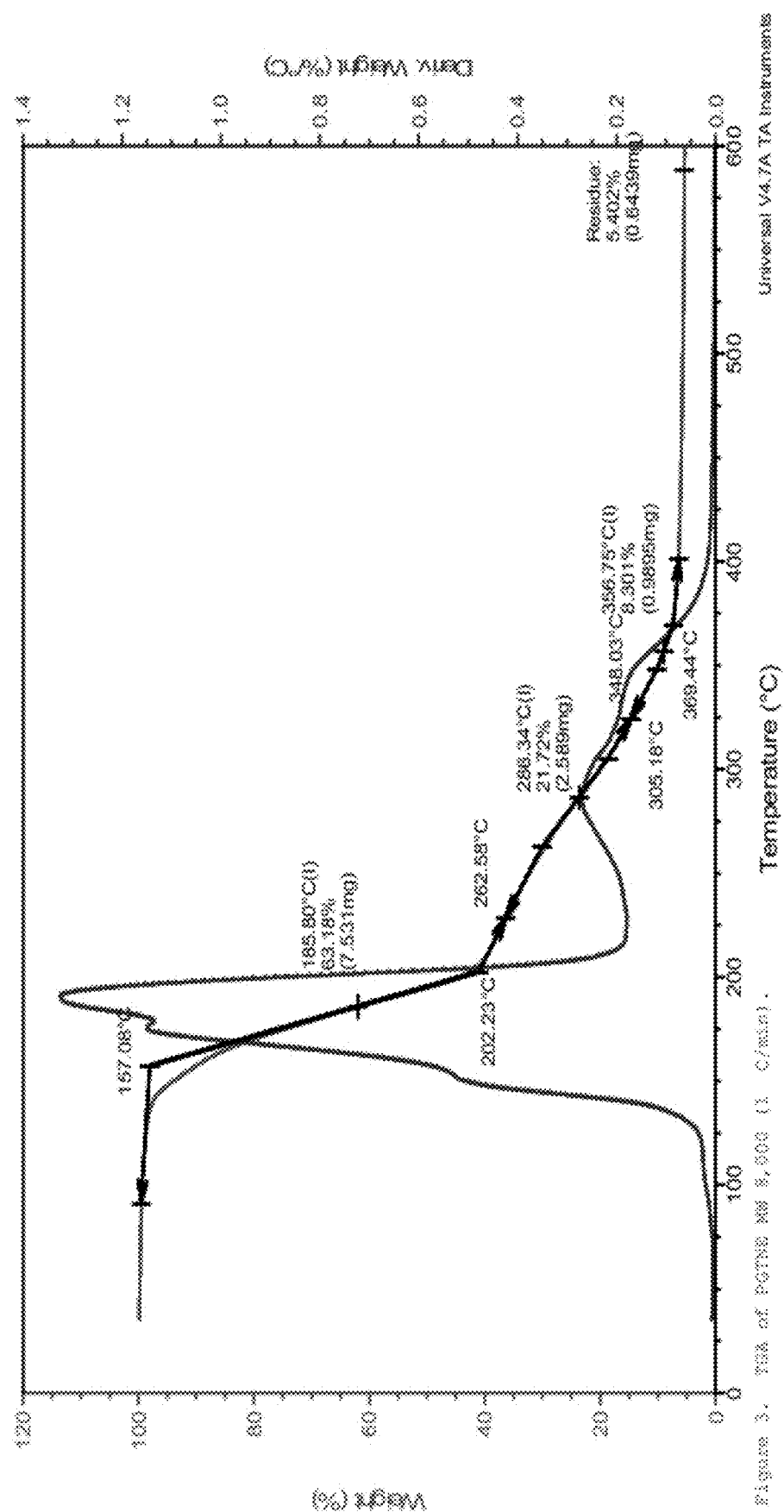

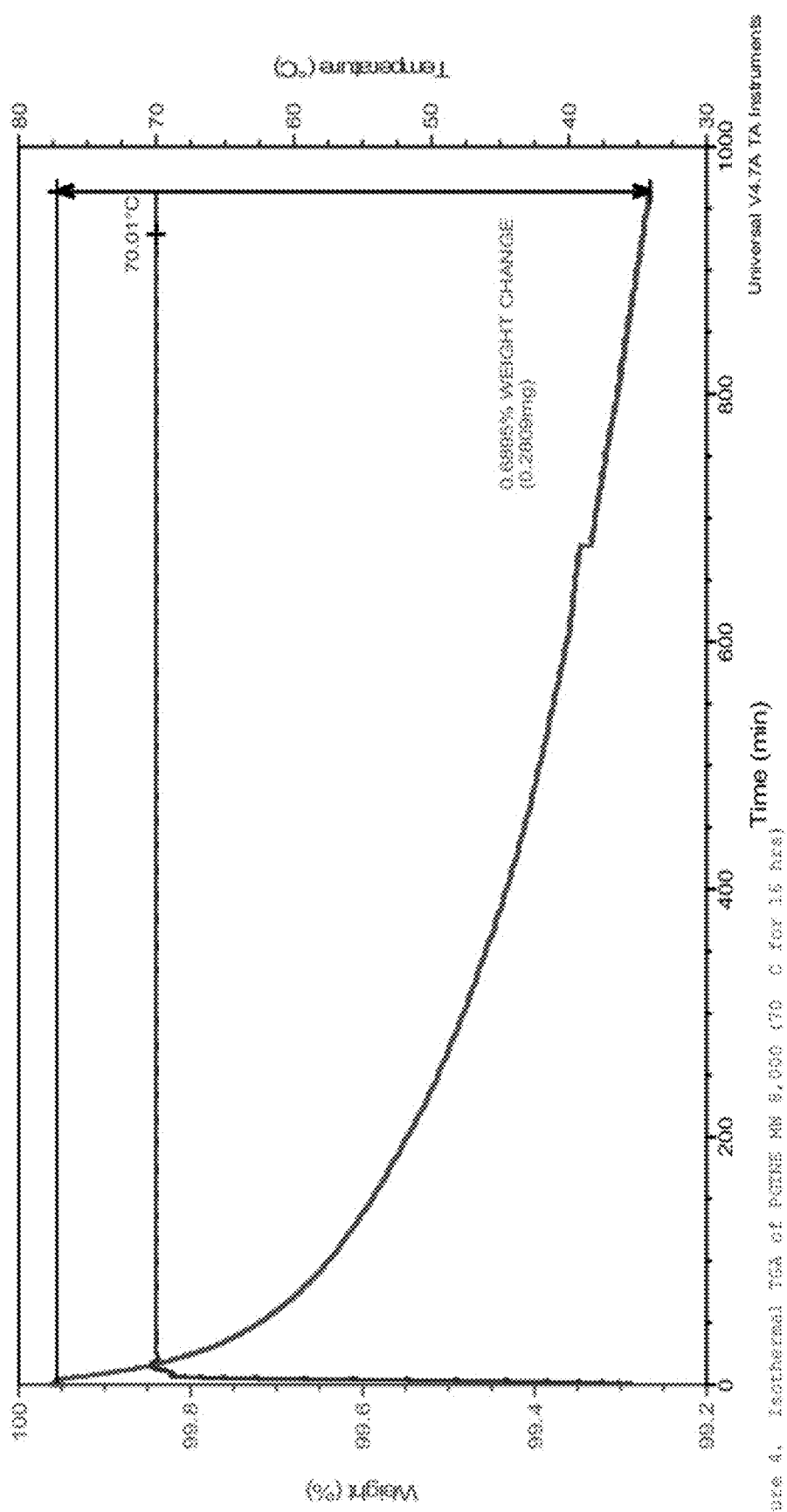
Figure 4. Isothermal TGA of PDMS MW 6,000 (70 C for 16 hrs)

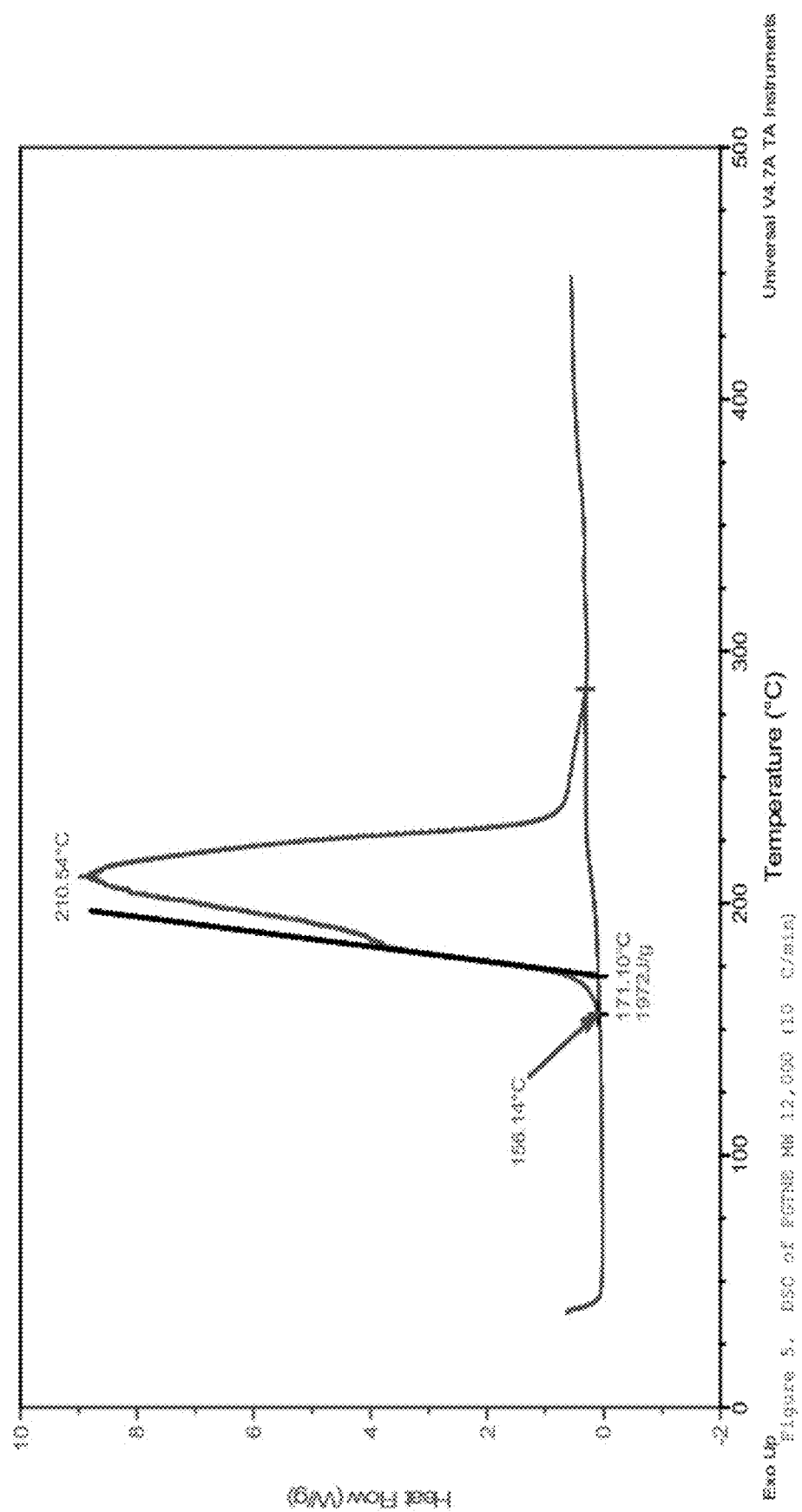

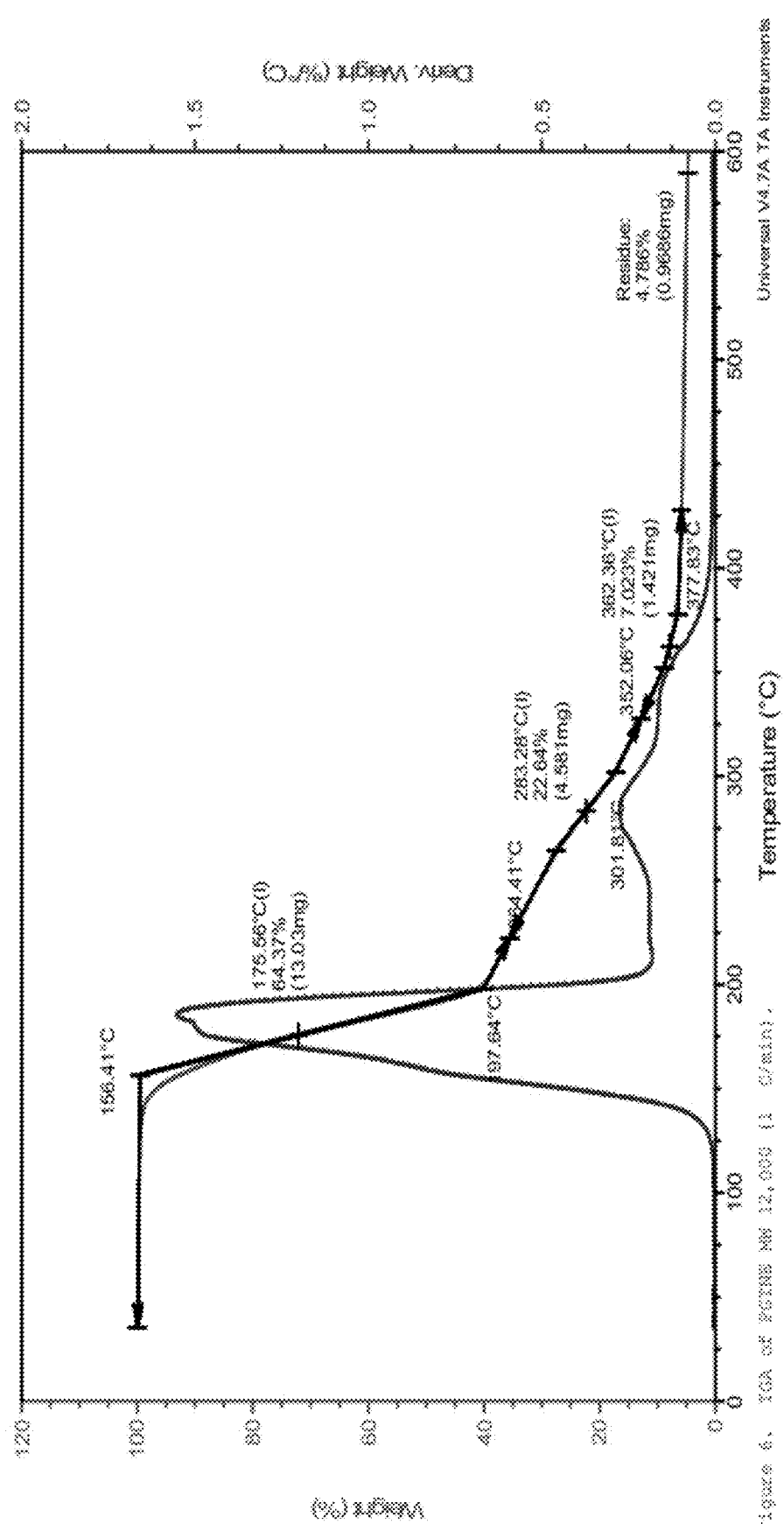

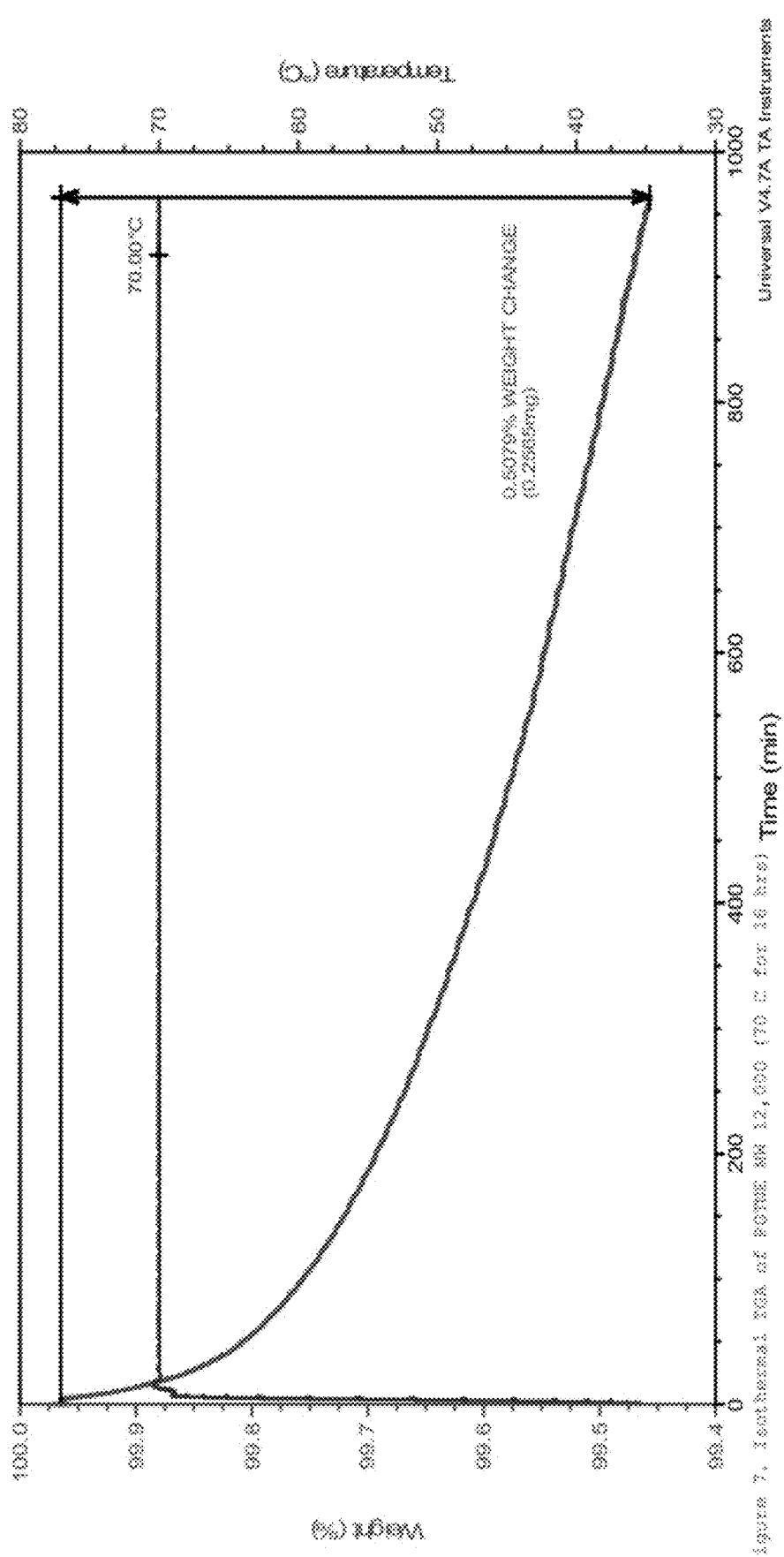

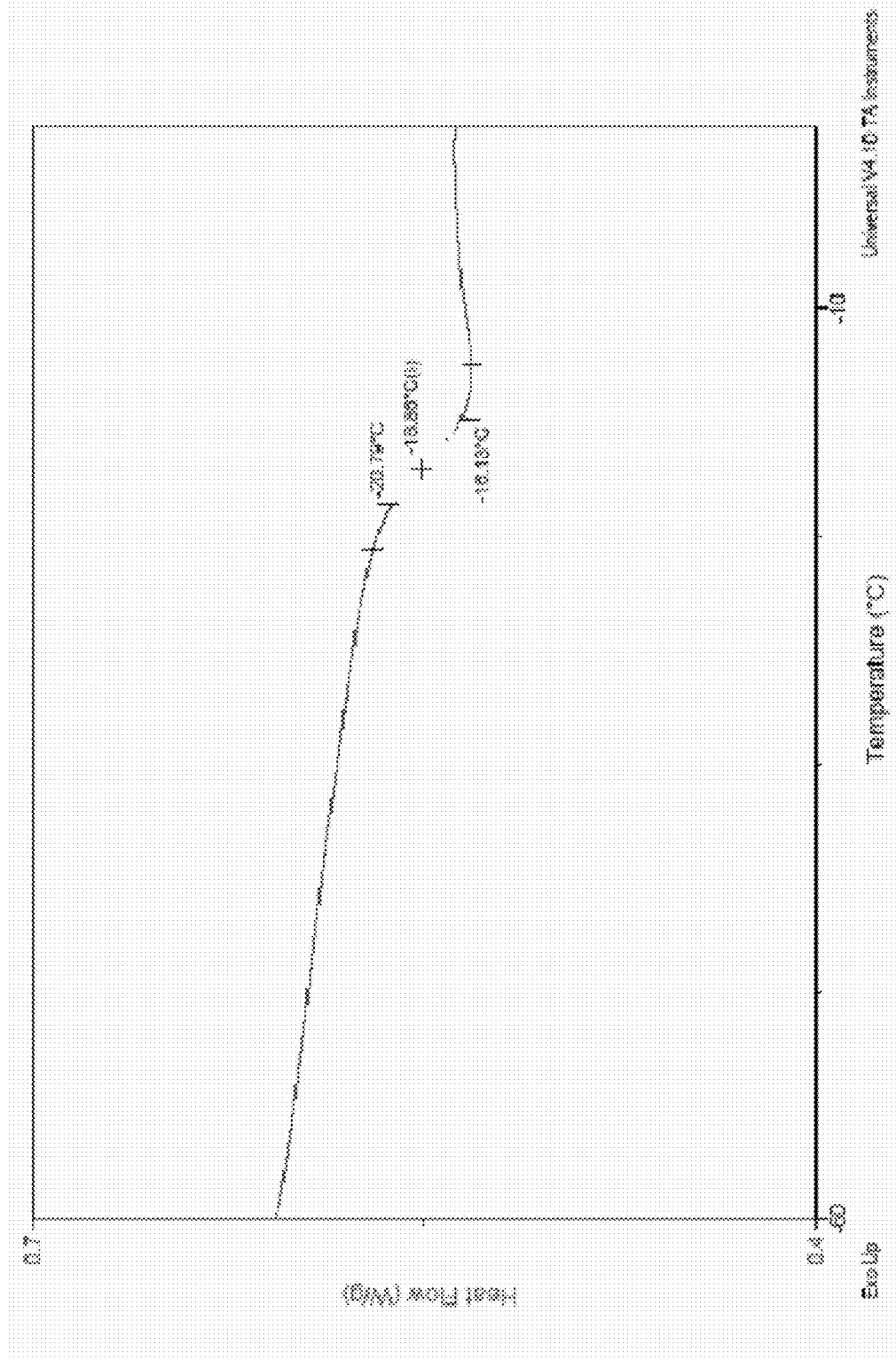
Figure 8. Low temperature DSC of PGTNE MW 3,000

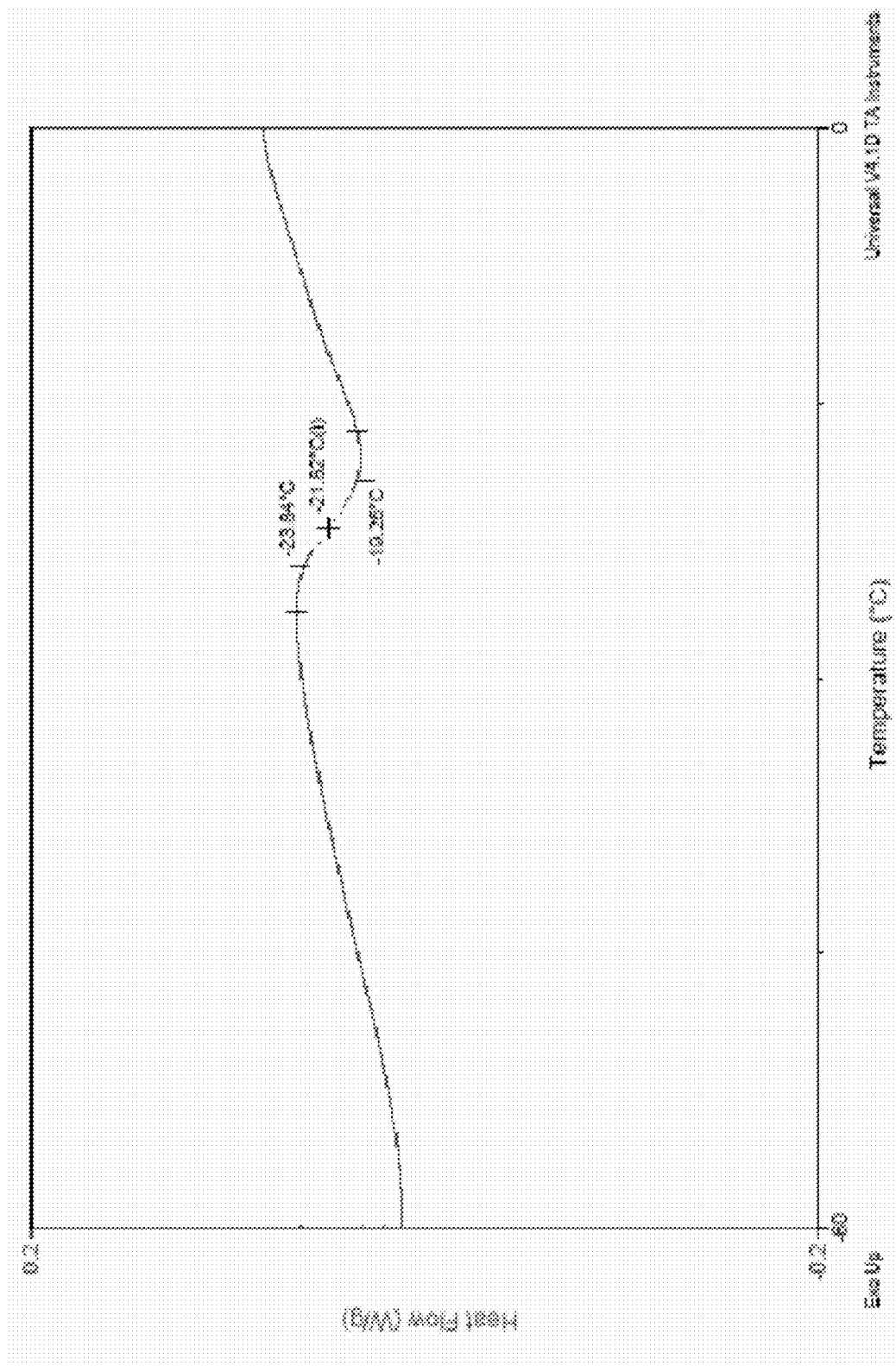
Figure 9. Low temperature DSC of poly(2,2-dinitropropyl glycidyl ether) (PDNPGE) 2,700.

SYNTHESIS AND POLYMERIZATION OF GLYCIDYL ETHERS

This invention was supported under Air Force SBIR Contracts FA9300-08-C-2101, FA9300-07-M-3112 and OSD-3 FA9300-07-M-3113.

BACKGROUND OF INVENTION

Hydroxy-terminated polybutadiene is widely used as a binder for polyurethane-based solid propellants because of its low viscosity and good low-temperature properties. The main chain in the isocyanate cured hydroxyl-terminated polybutadiene is hydrocarbon. Binders with energetic groups on the chain are desirable for increased performance.

One of the most-used approaches to the development of energetic propellant binders is to apply epoxide polymerizations to form oligomers, which are then treated with di- or polyisocyanates to form the polymer backbone. Examples include GAP (glycidyl azide polymer) and PGN (polyglycidyl nitrate), R. L. Willer and R. S. Day, *Proceedings of the APDA Joint International Symposium on the Compatibility of Plastics and Other Materials with Explosives, Propellants and Ingredients*, American Defense Preparedness Association, October, 1989, 258, Poly(Glycidyl Nitrate) Revisited; R. L. Willer, A. G. Stern, D. McGrath, 1990 *JANNAF Propulsion Meeting*, CPIA Publication 550, 3, 223, Poly(Glycidyl Nitrate) and Poly(Glycidyl Nitrate) Propellants. Epoxide polymerization has been developed to the extent that functionality and molecular weight can be controlled readily. Energetic groups can be added before the polymerization step, as in the case of PGN, or after, as with GAP.

PGN has been synthesized by the preparation of glycidyl nitrate, followed by Lewis acid polymerization, Willer, et. al., U.S. Pat. No. 5,120,827. GAP could not be synthesized in this way because glycidyl azide could not be polymerized cleanly, so it was prepared by polymerization of epichlorohydrin, followed by the displacement of chlorine atoms on the polymer by azide ions, M. B. Frankel, et. al., *GAP Polymer Demonstration*, Report RI/RD80-240, AD-B057531L, Rocketdyne, January 1981; J. C. Gray, et. al., *Energetic Ingredients for Gun Propellant*, Report RI/RD81-109, AD-B057310L, Rocketdyne, January 1981.

Readily available alcohols with high nitro content, such as 2,2-dinitropropanol and 2,2,2-trinitroethanol would appear to be logical choices for reacting with epichlorohydrin to give glycidyl ethers. However, under the basic conditions that are normally used to form glycidyl ethers, these alcohols lose formaldehyde to give the resonance-stabilized salts of 1,1-dinitroalkanes.

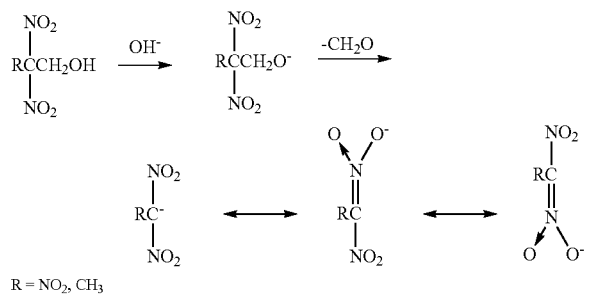

R = NO$_2$, CH$_3$

The inability to attach dinitropropyl groups directly to the glycidyl moiety prompted Kim, et. al., to synthesize dinitropropyl glycidyl carbonate, Kim, et. al., U.S. Pat. No. 6,706,849, and dinitropropyl glycidyl formal, Kim, et. al., U.S. Pat. No. 7,427,687, Kim, et. al., U.S. Pat. No. 7,208,637, and the corresponding polymers. The extra connecting groups result in substantial dilution of the nitro content of the polymers.

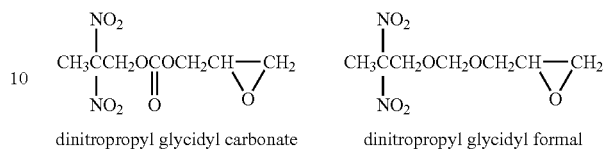

dinitropropyl glycidyl carbonate     dinitropropyl glycidyl formal

SUMMARY OF THE INVENTION

Novel glycidyl ethers having the generic formula:

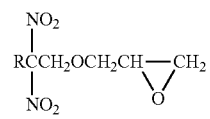

wherein R is a nitro, methyl, ethyl, cyano or chloride group, and the method of preparation.

Polyfunctional poly(glycidyl ethers) such as difunctional poly(glycidyl ethers) having the formula

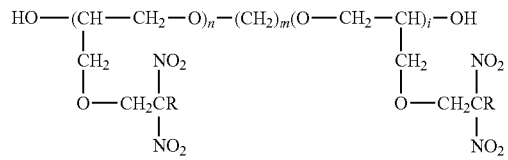

where R is nitro, methyl, ethyl, cyano or chloride, n and l are integers from 1 to about 100, and m is an integer from 2 to about 10, and the method of preparation; and Trifunctional poly(glycidyl ethers) having the formula:

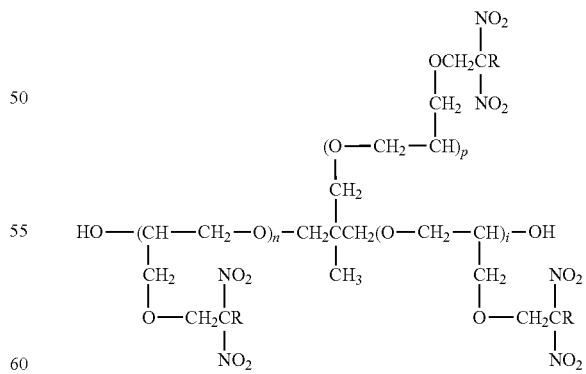

where R is nitro, methyl, ethyl, cyano or chloride, n, l and p are integers from 1 to about 100, and the method of preparation.

In the method of preparing allyl ethers having the generic formula:

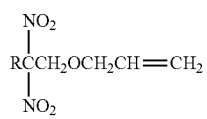

by reacting a polynitroalcohol having the formula:

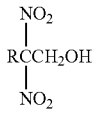

with allyl triflate under neutral conditions, wherein R is a nitro, methyl, ethyl, cyano or chloride group, the improvement wherein the allyl triflate is combined with the polynitroalcohol stepwise with the initial step being carried out at around 0° C. and subsequent addition of allyl triflate being carried out at around ambient temperature.

Novel polyurethanes based on the novel polyfunctional glycidyl ethers and the method of preparation.

DESCRIPTION OF PREFERRED EMBODIMENTS

This invention provides a novel method of alkylating dinitropropanol that avoids deformylation. It was found that 2,2-dinitropropanol, as well as 2,2,2-trinitroethanol can be alkylated with allyl triflate under neutral conditions to give the corresponding allyl ethers. Liberated triflic acid must be removed for the reaction to proceed, and it was found that a slurry of sodium sulfate functioned as a scavenging reagent for triflic acid. Allyl triflate was synthesized from allyl alcohol and triflic anhydride.

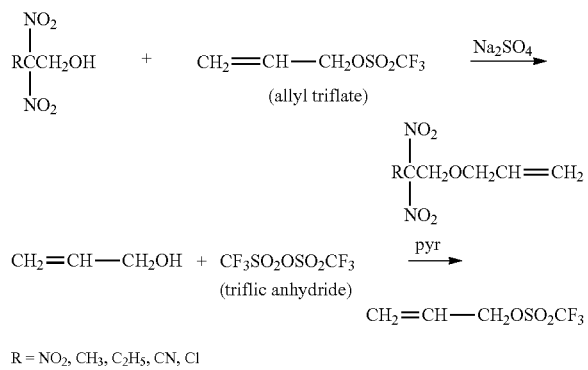

R = $NO_2$, $CH_3$, $C_2H_5$, CN, Cl

According to the present invention, both allyl 2,2-dinitropropyl ether and allyl 2,2,2-trinitroethyl ether were converted to the corresponding glycidyl ethers using m-chloroperbenzoic acid (MCPBA) in chloroform. Other common peroxidation reagents can also be used. This general approach to glycidyl ethers is useful for other alcohols, particularly those that cannot be reacted with epichlorohydrin because of sensitivity to base. Examples include 2-cyano-2,2-dinitroethanol, 2,2-dinitrobutanol, 2-chloro-2,2-dinitroethanol, etc.

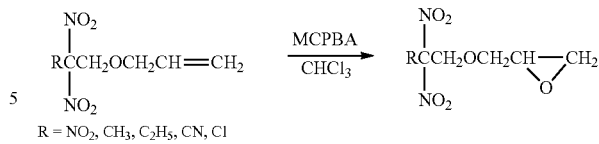

R = $NO_2$, $CH_3$, $C_2H_5$, CN, Cl

A. Preparation of Difunctional Polymer

Polymerizations of the epoxides were carried out in methylene chloride, using $BF_3$ etherate as a catalyst. The use of hydroxy initiators for epoxide polymerizations is well known. A difunctional alcohol, such as 1,4-butanediol as an initiator, controls the molecular weight of the product to give a difunctional polymer growing from the hydroxyl groups of the initiator.

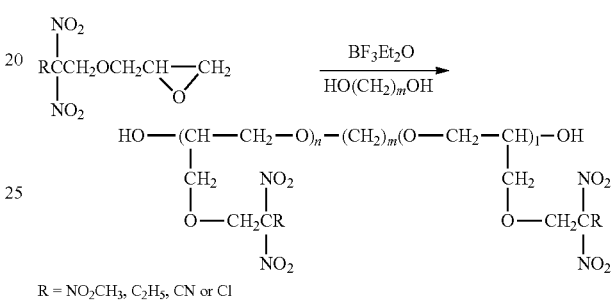

R = $NO_2$ $CH_3$, $C_2H_5$, CN or Cl n and l are integers from 1 to about 100 and m is an integer from 2 to about 10.

It is to be understood that the values of n and l may vary independently of one another.

B. Preparation of Trifunctional Polymer

The use of a triol, such as 1,1,1-tris(hydroxymethyl)ethane having the formula $CH_3$—C—$(CH_2$—$OH)_3$ as an initiator controls the molecular weight similarly and gives a trifunctional polymer.

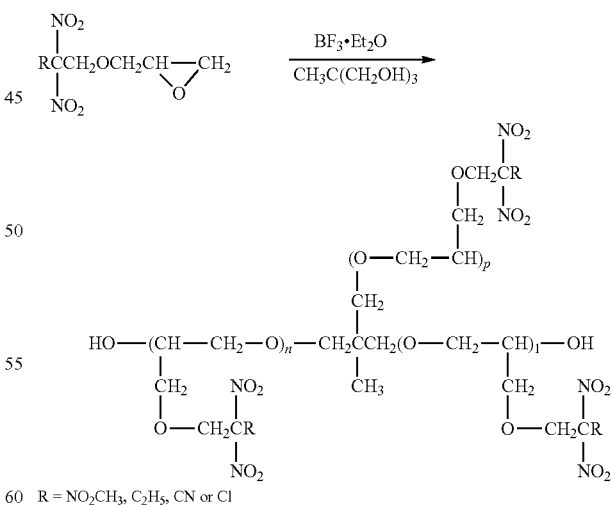

R = $NO_2$ $CH_3$, $C_2H_5$, CN or Cl n, l and p are integers from 1 to about 100.

It is understood that the values of n, l and p may vary independently of one another.

The foregoing reactions can also be carried out using other polyols such as glycerin and pentaerithritol.

A commonly used method for determining equivalent weights of hydroxyl-terminated oligomers is reaction with isocyanates. A. E. Oberth, AIAA 16th Aerospace Sciences Meeting Huntsville, Ala. January 1978, *Functionality determination in Hydroxyl-terminated Prepolymers*, reported a method using viscosity at varied hydroxyl-isocyanate ratios to determine the end point. The present invention utilizes a variation of this method, using IR observation of unreacted isocyanate for end-point determination. A mixture of the prepolymer, hexamethylene diisocyanate (HDI) and a catalytic amount of ferric acetyl acetonate was heated at 55° C., and the reaction was followed by IR using the isocyanate band at 2270 cm$^{-1}$. The ratio of HDI to prepolymer was adjusted until no isocyanate remained. Difunctional prepolymers were used, with theoretical molecular weights of 12000, 8000, and 2500, based on amount of initiator used for their preparation. The results are shown in Table 1.

TABLE 1

Equivalent weights of prepolymers.

| Prepolymer | MW theor. | Equivalent wt. theor. method | HDI |
|---|---|---|---|
| Difunctional Poly(glycidyl trinitroethyl ether) | 12000 | 6000 | 6000 |
| Difunctional Poly(glycidyl trinitroethyl ether) | 8000 | 4000 | 4000 |
| Difunctional Poly(glycidyl trinitroethyl ether) | 2500 | 1250 | 1300 |

THE DRAWINGS

FIG. 1 shows a qualitative test for high molecular weight polyurethane binder for propellants.

In FIG. 2 the Differential Scanning calorimetry ("DSC") of poly(glycidyl trinitroethyl ether) MW 8000 shows the onset of decomposition at 145° C. and peak at 207° C.

FIG. 3 shows the Thermogravimetric Analysis ("TGA") of poly(glycidyl trinitroethyl ether) MW 8000.

FIG. 4 shows the Isothermal Thermogravimetric Analysis at 70° C. of poly(glycidyl trinitroethyl ether) MW 8000.

In FIG. 5 the Differential Scanning calorimetry of poly (glycidyl trinitroethyl ether) MW 12000 shows the onset of decomposition at 156° C. and peak at 210.5° C.

FIG. 6 shows the Thermogravimetric Analysis of poly(glycidyl trinitroethyl ether) MW 12000.

FIG. 7 shows the Isothermal Thermogravimetric Analysis at Tat of poly(glycidyl trinitroethyl ether) MW 12000.

FIG. 8 shows the glass transition temperature by low temperature Differential Scanning calorimetry of poly(glycidyl trinitroethyl ether) MW 3000.

FIG. 9 shows the glass transition temperature by the low temperature Differential Scanning calorimetry of poly(2,2-dinitropropyl glycidyl ether) MW 2700.

The isocyanate-cured gumstocks yielded polyurethanes which were soft gummy materials. When a spatula was dipped into the gumstock and lifted, the material stretched extensively before breaking. This technique is commonly used as a qualitative test for high molecular weight polymers. See FIG. 1.

Impact, friction and ESD tests for 8000 molecular weight PGTNE, compared to RDX as a standard, are shown in Table 2. The DSC of 8,000 molecular weight PGTNE (FIG. 2) shows onset of decomposition at 145° C. and peak at 207° C., and the TGA is shown in FIG. 3. Isothermal TGA at 70° C. for 16 hrs shows 0.69% weight loss (FIG. 4).

Impact, friction and ESD tests for 12,000 molecular weight PGTNE, compared to RDX as a standard, are shown in Table 3. The DSC of 12000 molecular weight PGTNE (FIG. 5) shows onset of decomposition at 156° C. and peak at 210.5° C., and the TGA is shown in FIG. 6. Isothermal TGA at 70° C. for 16 hrs shows 0.51% weight loss (FIG. 7).

Low temperature properties are important for propellant performance; glass transition temperatures (Tg) were determined by low-temperature DSC. The Tg of 3,000 molecular weight PGTNE was −18.86° C., and that of 2,700 molecular weight poly(2,2-dinitropropyl glycidyl ether), PDNPGE, was −21.82° C. (FIGS. 8 and 9)

TABLE 2

PGTNE 8000 Sensitivity testing

| Hazard | PGTNE 8K MW | RDX |
|---|---|---|
| Impact, kg-cm | 140 | 49 |
| Friction, psi @ drop angle, ° threshold | >100 @ 90° | 1200 @ 90° |
| ESD, J @ 5 kv (threshold) | >1.0 | 0.38 |

TABLE 3

Sensitivity testing of PGTNE 12,000

| Hazard | PTNEGE 12K MW | RDX |
|---|---|---|
| Impact, kg-cm | 140 | 49 |
| Friction, psi @ drop angle, ° threshold | >100 @ 90° | 1200 @ 90° |
| ESD, J @ 5 kv (threshold) | >1.0 | 0.38 |

The following examples will serve to illustrate the invention.

EXAMPLE 1

Synthesis of allyl 2,2-dinitropropyl ether

A solution of allyl alcohol (16 g, 276 mmol) and 2-chloropyridine (32 g, 282 mmol) in methylene chloride (100 ml) was added over 30 min to a stirred solution of trifluoromethanesulfonic anhydride (78 g, 277 mmol) in methylene chloride (200 ml) at 0° C. The mixture was stirred in an ice bath for 3 h, and then filtered cold to remove the salt byproduct. The brown allyl triflate solution was stored in a freezer for use in the following reaction. A solution of 2,2-dinitropropanol (24 g, 160 mmol) in methylene chloride (100 ml) was added, with ice bath cooling, over 15 min to a stirred mixture of one-half of the allyl triflate solution and anhydrous sodium sulfate (50 g). The ice bath was removed. After the mixture was stirred at room temperature for 17 h, sodium sulfate (40 g) and half of the remaining allyl triflate solution were added. After another 8 his of stirring at ambient temperature, another 40 g portion of sodium sulfate and the remaining allyl triflate solution were added, and stirring was continued for 17 h. The mixture was filtered. The solution was washed with saturated sodium bicarbonate solution and with water. The solution was dried over magnesium sulfate and solvent was removed under vacuum. The brown liquid residue was distilled to give 25.7 g of allyl 2,2-dinitropropyl ether, by 50° C./0.1 mm Hg, 84% yield based on dinitropropanol: HNMR (acetone-d$_6$): 2.20 (s, 3H), 4.15 (t of d, 2H), 4.37 (s, 2H), 5.22 (AB quartet, of d, 1H), 5.30 (AB quartet of d, 1H), 5.90 (m, 1H) ppm; IR (neat): 2890 (m), 1573 (br, vs), 1469 (m), 1445 (m), 1424 (m), 1401 (m), 1383 (m), 1349 (m), 1328 (s), 1273 (w), 1230 (w), 1195 (m), 1099 (br, s), 989 (s), 939 (s), 869 (m), 848 (m), 776 (w), 736 (w) cm$^{-1}$.

When allyl triflate and 2,2-dinitropropanol were combined at once at ambient temperature according to Beard, et. al., "Synthesis of Some Novel Trifluoromethansulfonates and Their Reactions with Alcohols", *J. of Org. Chem.*, 38(21): 3077-4468 (1973) at pp. 3673 and 3676, the yield of the ether was 53%.

EXAMPLE 2

Synthesis of allyl 2,2,2-trinitroethyl ether

A solution of allyl alcohol (30 g, 520 mmol) and 2-chloropyridine 60 g, 530 mmol) in methylene chloride (100 ml) was added over 60 min to a stirred solution of trifluoromethanesulfonic anhydride (147 g, 520 mmol) in methylene chloride (350 ml) at 0° C. The mixture was stirred at 0° C. for 3 h and then filtered. The brown allyl triflate solution was stored in a freezer for use in the following reaction. A solution of trinitroethanol (58 g, 320 mmol) in methylene chloride (300 ml) was added, with ice bath cooling, over 30 min to a stirred mixture of one-half of the allyl triflate solution and anhydrous sodium sulfate (80 g). The ice bath was removed. After the mixture was stirred at room temperature for 17 h, sodium sulfate (40 g) and half of the remaining allyl triflate solution were added. After another 24 hrs of stirring at ambient temperature, another 40 g portion of sodium sulfate and the remaining allyl triflate solution were added, and stirring was continued for 24 h. The mixture was filtered. The solution was washed with saturated sodium bicarbonate solution and with water. The solution was dried over magnesium sulfate and solvent was removed under vacuum. The brown liquid residue was chromatographed using silica gel and methylene chloride, followed by distillation to give allyl trinitroethyl ether, bp. 45° C./0.1 mm Hg, yield 60% (42.7 g) based on the trinitroethanol: HNMR (acetone-d$_6$): 4.30 (t of d, 2H), 5.13 (s, 2H), 5.26 (AB quartet of d, 1H), 5.33 (AB quartet of d, 1H), 5.90 (m, 1H) ppm; IR (neat): 2927 (w), 2877 (w), 1597 (br, vs), 1447 (w), 1425 (w), 1347 (w), 1305 (s), 1194 (w), 1123 (br, m), 1029 (w), 995 (w), 938 (m), 879 (w), 856 (w), 804 (m), 783 (m), 732 (w) cm$^{-1}$.

When allyl triflate and trinitroethanol were combined at once at ambient temperature according to Beard, et. al., supra, the yield of the ether was 33%.

EXAMPLE 3

Synthesis of glycidyl 2,2,2-trinitroethyl ether (GTNE)

A solution of allyl trinitroethyl ether (111 g, 502 mmol) in chloroform (100 ml) was added to the mechanically stirred mixture of m-chloroperoxybenzoic acid (102 g, 590 mmol) and chloroform (450 ml). The mixture was refluxed at 70° C. for 6 h under nitrogen. The mixture was cooled with an ice bath for 30 min and filtered. The filtrate was concentrated and additional precipitate was filtered out. The filtrate was diluted with methylene chloride, washed with 10% sodium thiosulfate, saturated sodium bicarbonate, water and dried. Solvent was removed under vacuum. The golden yellow liquid residue (109 g) was chromatographed in portions using silica gel and methylene chloride to give 72 g (60% yield) of glycidyl trinitroethyl ether: $^1$HNMR (CDCl$_3$) 2.64 (d of d, 1H), 2.87 (t, 1H), 3.22 (m, 1H), 3.53 (d of d, 1H), 4.15 (d of d, 1H), 4.85 (AB quartet, 2H) ppm; IR (neat): 3067 (w), 3006 (m), 2932 (m), 1591 (br, vs), 1454 (m), 1340 (m), 1305 (s), 1254 (m), 1161 (m), 1138 (s), 1082 (m), 1032 (w), 988 (w), 945 (w), 900 (m), 880 (m), 855 (m), 804 (s), 782 (m) cm$^{-1}$.

Calcd for C$_5$H$_7$N$_3$O$_8$: C, 25.33; H, 2.98; N, 17.72. Found: C, 25.28; H, 2.97; N, 16.52%.

Any of the well known peroxidizing agents can be used in lieu of m-chloro-peroxy benzoic acid.

EXAMPLE 4

Synthesis of 2,2-dinitropropyl glycidyl ether (DNPGE)

A solution of allyl 2,2-dinitropropyl ether (30 g, 160 mmol) in chloroform (50 ml) was added to a mechanically stirred mixture of m-chloroperoxybenzoic acid (35 g, 200 mmol) and chloroform (300 ml). The mixture was refluxed at 70° C. for 6 h under nitrogen. The mixture was cooled with an ice bath for 30 min and filtered. The filtrate was concentrated and additional precipitate was filtered out. The filtrate was diluted with methylene chloride, washed with 10% sodium thiosulfate, saturated sodium bicarbonate, water and dried. Solvent was removed under vacuum. The yellow liquid residue (31 g) was chromatographed using silica gel and methylene chloride to give 21 g (63% yield) of 2,2-dinitropropyl glycidyl ether: HNMR (CDCl$_3$): 2.19 (s, 3H), 2.57 (d of d, 1H), 2.79 (t, 1H), 3.10 (m, 1H), 3.40 (d of d, 1H), 3.91 (d of d, 1H), 4.35 (AB quartet, 2H) ppm; IR (neat): 3063 (w), 3005 (m), 2927 (m), 1566 (br, vs), 1468 (m), 1443 (m), 1402 (m), 1380 (m), 1329 (s), 1280 (w), 1254 (w), 1232 (w), 1161 (m), 1112 (br, s), 999 (w), 967 (w), 905 (m), 849 (m), 764 (m) cm$^{-1}$.

Calcd for C$_6$H$_{10}$N$_2$O$_6$: C, 34.96; H, 4.89; N, 13.59. Found: C, 34.40; H, 4.71; N, 13.15%.

EXAMPLE 5

Synthesis of difunctional poly(glycidyl 2,2,2-trinitroethyl ether), MW 12,000 (PGTNE)

A mixture of 1,4-butanediol (0.6197 g, 6.886 mmol) and BF$_3$ etherate (0.9778 g, 6.889 mmol) was stirred at room temperature under nitrogen for 2 h. Ether was removed under 0.1 mm vacuum at 0° C. for 0.5 h and room temperature for 5 h. A brown liquid diol-BF$_3$ complex (1.0948 g, 6.886 mmol) was obtained.

A solution of glycidyl 2,2,2-trinitroethyl ether (34.30 g) in methylene chloride (35 ml) was added, over a 4 h period, to a slurry of 1,4-butanediol-BF$_3$ complex (0.4558 g, 2.867 mmol), in methylene chloride (6.5 ml) at 0° C. The resulting solution was stirred at 0-5° C. for 5 h and then at room temperature for 15 h. The light-brown solution was diluted with methylene chloride (100 ml), washed with saturated sodium bicarbonate, water and dried over magnesium sulfate. The solvent was removed under vacuum to give 33.2 g of poly(glycidyl trinitroethyl ether) as a viscous golden yellow liquid: HNMR (acetone-d$_6$): 1.60, 3.52, 3.54, 3.58, 5.20 ppm; IR (neat): 3464 (br, w), 2932 (s), 2886 (s), 1604 (br, vs), 1463 (m), 1348 (m), 1305 (br, vs), 1120 (vbr, vs), 956 (w), 880 (m), 856 (m), 804 (s), 782 (s), 735 (m) cm$^{-1}$.

Calcd: C, 25.53; H, 3.04; N, 17.59. Found: C, 25.00; H, 3.80; N, 17.60%.

EXAMPLE 6

Synthesis of difunctional poly(glycidyl 2,2,2-trinitroethyl ether), MW 8,000

A solution of glycidyl 2,2,2-trinitroethyl ether (11.0 g) in methylene chloride (10 ml) was added over 1 h to a slurry of 1,4-butanediol-BF$_3$ (0.2165 g, 1.380 mmol) in methylene chloride (2.0 ml) at 0° C. The reaction condition and workup were same as those for Example 5. The solvent was removed under vacuum to give 10.7 g of MW 8,000 polymer.

Calcd: C, 25.36; H, 3.29; N, 17.59. Found: C, 26.00; H, 3.32; N, 17.17%.

EXAMPLE 7

Synthesis of difunctional poly(glycidyl 2,2,2-trinitroethyl ether), MW 2,500

A solution of glycidyl 2,2,2-trinitroethyl ether (1.98 g) in methylene chloride (2.0 ml) was added in 25 min to a mixture of 1,4-butanediol-BF$_3$ (0.1249 g, 0.790 mmol) in methylene chloride (0.5 ml) at 0° C. The reaction condition and workup were same as those for Example 5. The solvent was removed under vacuum to give 2.0 g of MW 2,500 polymer.

EXAMPLE 8

Synthesis of trifunctional poly(glycidyl 2,2,2-trinitroethyl ether), MW 6,000

A mixture of 1,1,1-tris(hydroxymethyl)ethane (40.0 mg, 0.33 mmol) and BF$_3$ etherate (46.3 mg, 0.33 mmol) was stirred at room temperature under nitrogen for 2 h. Ether was removed at 0.1 mm Hg at 0° C. for 0.5 h and at room temperature for 5 h. A solution of glycidyl 2,2,2-trinitroethyl ether (2.0 g) in methylene chloride (1.0 ml) was added in 25 min to a slurry of 1,1,1-tris(hydroxymethyl)ethane-BF$_3$ in methylene chloride (0.5 ml) at 0° C. The reaction condition and workup were same as those for Example 5. The solvent was removed under vacuum to give 2.0 g of MW 6,000 polymer.

EXAMPLE 9

Synthesis of difunctional poly(2,2-dinitropropyl glycidyl ether), MW 4,000 (PDNPGE)

A solution of 2,2-dinitropropyl glycidyl ether (2.0 g) in methylene chloride (2 ml) was added in 15 min to a slurry of 1,4-butanediol-BF$_3$ (0.079 g, 0.5 mmol) in methylene chloride (0.5 ml) at 0° C. The resultant solution was stirred at 0-5° C. for 5 h, then at room temperature for 15 h. The light-brown solution was diluted with methylene chloride (30 ml), washed with saturated sodium bicarbonate, water and dried over magnesium sulfate. The solvent was removed under vacuum to give 2.0 g of poly(2,2-dinitropropyl glycidyl ether) as a light-brown liquid: DSC at 10° C./min. exotherm onset 214° C.; HNMR (CDCl$_3$): 1.60, 218, 3.47, 3.60, 4.32 ppm; IR (neat): 3463 (br, w), 2926 (s), 2886 (S), 1573 (br, vs), 1470 (s), 1446 (s), 1391 (s), 1353 (s), 1329 (s), 1278 (m), 1231 (m), 1119 (br, vs), 1011 (m), 864 (m), 848 (m), 775 (m), 734 (w), 673 (m) cm$^{-1}$.

EXAMPLE 10

Synthesis of difunctional poly(2,2-dinitropropyl glycidyl ether), MW 2,500

A solution of 2,2-dinitropropyl glycidyl ether (2.0 g) in methylene chloride (2 ml) was added in 15 min to a slurry of 1,4-butanediol-BF$_3$ (0.126 g, 0:8 mmol) in methylene chloride (0.5 ml) at 0° C. The reaction condition and workup were same as those for Example 9. The solvent was removed under vacuum to give 2.0 g of MW 2,500 polymer.

It is, intended that other alkane diols can be used which include both branched and straight chain diols such as pentane diol, hexane diol and the like.

EXAMPLE 11

Preparation of Polyurethane Gumstocks a. A solution of 1.3016 g (0.651 meq) of trifunctional poly(trinitroethyl glycidyl ether) (MW 6,000), 54.9 mg (0.654 meq) of hexamethylene diisocyanate in 0.58 g of toluene and 3 drops of 1% ferric acetyl acetonate in toluene was heated at 50° C. for 17 h. The residual solvent was removed under vacuum.

b. A solution of 1.0520 g (0.8416 meq.) of difunctional poly(trinitroethyl glycidyl ether) (MW 2,500), 71.4 mg (0.850 meq) of hexamethylene diisocyanate in 0.48 g of toluene and 3 drops of 1% ferric acetyl acetonate in toluene was heated at 50° C. for 17 h.

The residual solvent was removed under vacuum.

Other polyiisotyanates such as toluene diisocyanate can be used in lieu of hexamethylene diisocyanate.

The invention claimed is:

1. Novel glycidyl ethers having the generic formula:

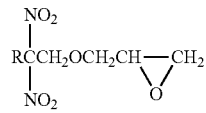

wherein R is a nitro, methyl, ethyl or cyano group.

2. Glycidyltrinitroethyl ether.
3. 2,2-dinitropropyl glycidyl ether.
4. The method of preparing the glycidyl ethers having the formula:

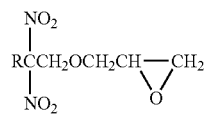

which comprises converting the corresponding allyl ether having the formula:

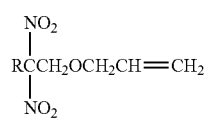

using a peroxidizing agent in chloroform, wherein R is a nitro, methyl, ethyl or cyano group.

* * * * *

UNITED STATES PATENT AND TRADEMARK OFFICE
CERTIFICATE OF CORRECTION

| | | |
|---|---|---|
| PATENT NO. | : 8,318,959 B1 | Page 1 of 1 |
| APPLICATION NO. | : 13/343132 | |
| DATED | : November 27, 2012 | |
| INVENTOR(S) | : Kurt Baum et al. | |

It is certified that error appears in the above-identified patent and that said Letters Patent is hereby corrected as shown below:

Column 1, Line 46: formaldehyde to give the ~~resonance-stabilizedsalts~~ resonance-stabilized salts of 1.1-

Signed and Sealed this

Twenty-ninth Day of January, 2013

David J. Kappos
*Director of the United States Patent and Trademark Office*